(12) United States Patent
Baturin et al.

(10) Patent No.: US 10,739,473 B2
(45) Date of Patent: Aug. 11, 2020

(54) IMAGE FUSION IN MULTI-LAYER FLAT PANEL IMAGER

(71) Applicant: Varian Medical Systems, Inc., Palo Alto, CA (US)

(72) Inventors: Pavlo Baturin, Santa Clara, CA (US); Adam Shar Wang, Menlo Park, CA (US); Liangjia Zhu, Menlo Park, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 2 days.

(21) Appl. No.: 16/237,520

(22) Filed: Dec. 31, 2018

(65) Prior Publication Data

US 2020/0209411 A1    Jul. 2, 2020

(51) Int. Cl.
*G01T 1/24* (2006.01)
*G01T 1/20* (2006.01)
*A61B 6/00* (2006.01)

(52) U.S. Cl.
CPC .......... *G01T 1/2002* (2013.01); *A61B 6/5205* (2013.01); *A61B 6/5235* (2013.01); *G01T 1/2018* (2013.01)

(58) Field of Classification Search
CPC ..... G01T 1/2018; G01T 1/2008; G01T 1/241; G01T 1/242; G01T 1/24; G21K 4/00; H01L 27/1464; H01L 25/0655; H01L 27/14636; H01L 27/14663; A61B 6/4035
See application file for complete search history.

(56) References Cited

U.S. PATENT DOCUMENTS

| 7,671,342 B2 | 3/2010 | Bani-hashemi et al. |
| 10,444,378 B1 * | 10/2019 | Morf .................... A61B 6/4035 |
| 2008/0011960 A1 | 1/2008 | Yorkston et al. |
| 2011/0303849 A1 | 12/2011 | Tredwell et al. |
| 2019/0331806 A1 * | 10/2019 | Morf .................... H01L 31/115 |

OTHER PUBLICATIONS

Baturin, Pavlo, et al. "Spectral CT Imaging of Vulnerable Plaque with Two Independent Biomarkers." *Physics in Medicine and Biology*, vol. 57, Jun. 8, 2012, pp. 4117-4138.
International Search Report and Written Opinion dated Apr. 20, 2020 for corresponding PCT Application No. PCT/US2019/068352.

* cited by examiner

*Primary Examiner* — Don K Wong
(74) *Attorney, Agent, or Firm* — Vista IP Law Group, LLP

(57) ABSTRACT

An imaging apparatus includes: a first scintillator layer configured to provide first image signals with a first quantum efficiency and a first spatial resolution; a second scintillator layer configured to provide second image signals with a second quantum efficiency and a second spatial resolution, wherein the first quantum efficiency is lower than the second quantum efficiency, but the first spatial resolution is higher than the second spatial resolution; and an image combiner configured to combine the first image signals and the second image signals.

20 Claims, 8 Drawing Sheets

IMAGE FUSION IN MULTI-LAYER FLAT PANEL IMAGER

FIELD

The field of the application relates to medical imaging, and more particularly, to imaging devices for providing medical images and methods of processing image signals from such imaging devices.

BACKGROUND

Imaging devices, such as an x-ray imager, have been used for diagnostic and treatment purposes. One type of x-ray imager is a diagnostic imager configured to operate with a diagnostic radiation source. Another type of x-ray imager is a high Detective Quantum Efficiency (DQE) detector that is configured for use with a treatment radiation source. An x-ray imager may also be configured for use with both diagnostic radiation beam and treatment radiation beam.

Creating a high DQE electronic portal imaging device (EPID) presents a significant technical challenge. One approach uses thick pixilated scintillator arrays that are coupled to a matrix of photodiodes. Incoming x-ray photons deposit energy into the scintillator which then produces optical photons via luminescence. These optical photons, which originate with random polarizations and direction vectors after the luminescence events, are transported throughout the scintillator where they can be reflected, refracted and scattered out of borders. Eventually, many photons will cross the boundary of the scintillator, and will reach the EPID's photodiodes. The photodiodes convert the photons into electrical current for readout and digitization. Despite the promise of the technology, performance of current EPIDs may be inadequate.

Current EPIDs employed in the field of radiotherapy utilize standard indirect flat panel design that includes a thin gadolinium oxysulfide (GOS) scintillator. The thickness of GOS scintillator is typically kept small to preserve the spatial resolution. The small thickness of the scintillator and high energies of megavoltage photon beams, used in radiotherapy field, yield low X-ray absorption within a scintillator. Low X-ray absorption limits the number of optical light produced in the scintillator and measured subsequently by a photo-diode matrix. Although a spatial resolution of the resulting digital image stays high, the signal to noise ratio (SNR) is degraded due to poor absorption characteristics. Current EPIDs suffer from low DQE (e.g., ~1.8%) for MV imaging. Imaging tasks with such low quantum efficiency detectors are not very practical due to low contrast, especially when imaging soft tissue. Creation of an imaging device with a high DQE in the megavoltage range remains an important problem in the radiotherapy field.

One possible approach to increasing quantum efficiency (QE) is to try to make several identical detection layers for the EPID, and then stack them together. One example of such implementation is to have several identical detection layers folded under each other with the aim to catch unabsorbed X-rays in superior detection layers. While such configuration can increase DQE, manufacturing expense may make such a solution impractical. For example, if the EPID has four identical detection layers, the total DQE of the EPID can increase up to 4 times compared to a single layer EPID. The production cost may also increase up to four times, making higher efficiency benefits less attractive.

SUMMARY

An imaging apparatus having multiple radiation-detecting layers is described herein. The imaging apparatus may have a first scintillator layer (e.g., Gadolinium oxysulfide (GOS)-based scintillator) that provides first image signals, and a second scintillator layer (e.g., glass-based scintillator, such as LKH5 scintillator) that provides second image signals. The first scintillator layer together with its associated photodiodes may provide a low-QE and high spatial resolution for the first image signals (forming a first image), and the second scintillator layer together with its associated photodiodes may provide a high-QE and low spatial resolution for the second image signals (forming a second image). Thus, a first image formed by the first image signals will be a noisy image with higher frequency details compared to a second image formed by the second image signals, while the second image will be a blurry image with a lower noise compared to the first image. The first scintillator layer may be thinner than the second scintillator layer.

The embodiments described herein are not limited to a two-layer detector configuration and two-image fusion. The detector can comprise more than two scintillator layers, which, as a result, would provide a plurality of digital images, which can be combined in the manners described herein. In addition, the choice of scintillator described is not limited to GOS and glass-like materials. The materials and dimensions of scintillators can be selected such that the X-ray absorption and light output properties can yield digital images with inherently different signal-to-noise and resolution characteristics. The scintillator could be made of ceramic, plastic, glass, or any other suitable material that exhibits scintillating properties. Also, scintillators can be made of clear or turbid material, as well as being structured in a pixelated or non-pixelated (slab) form.

Embodiments described herein teach how to combine these two inherently different images (i.e., (1) a high resolution (sharp) and low-efficiency (low signal-to-noise) image and (2) a low resolution (blurry) high-efficiency (high signal-to-noise) image) into one "fused" image. To combine the first and second image signals, several image fusion techniques may be employed in different embodiments. By means of non-limiting examples, the image fusion technique may take advantage of detector imaging characteristics, such as modulation transfer function (MTF), noise power spectrum (NPS), DQE, or any combination of the foregoing. In some embodiments, the first and second image signals may be combined in a way that maximizes an image's SNR and/or that minimizes spatial resolution losses (that may occur during image fusion).

In some embodiments, images from the multiple layers may be combined via weighted summation. The weighting may be dependent on spatial frequency, with the weights w(f) chosen to maximize SNR of the combined image for all spatial frequencies f. This effectively maximizes the combined image's DQE, which is a measure of image quality as a function of spatial frequency. The weights w(t) may be chosen based on the performance of each detector layer, where performance is dictated by spatial resolution (relating to MTF) and noise (relating to NPS). In some cases, the weights may be chosen to maximize DQE in the combined image. For example, if image n has performance described by $DQE_n(f)=MTF_n^2(f)/NPS_n(f)$, then the optimal linear weighting for image n is $w_n(f)=[(MTF_n/NPS_n)/\Sigma_n(MTF_n/NPS_n)](f)$, where the summation is over all images. The combined image is then: $Im'(f)=\Sigma_n w_n(f) \cdot Im_n(f)$, where the linear weights give Im' the highest possible DQE for all frequencies. Each spatial frequency can be selected using 2D image filters. Using the two-layer (e.g., GOS+glass-based scintillators) example, the predicted MTF and NPS of each of the two images (from the respective two scintillators) may be used to determine optimal linear weights w(f) for each image. These weights result in a desirable (e.g., maximum) DQE across all frequencies.

Some exemplary imaging apparatus include: a first scintillator layer configured to provide first image signals with a first quantum efficiency and a first spatial resolution; a second scintillator layer configured to provide second image signals with a second quantum efficiency and a second spatial resolution, wherein the first quantum efficiency is lower than the second quantum efficiency, but the first spatial resolution is higher than the second spatial resolution; and an image combiner configured to combine the first image signals and the second image signals.

Optionally, the image combiner is configured to combine the first image signals and the second image signals in a way that increase signal-to-noise ratio while reducing spatial resolution loss.

Optionally, the image combiner is configured to combine the first image signals and the second image signals based on frequency-dependent weighting.

Optionally, the image combiner is configured to combine the first image signals and the second image signals based on frequency-dependent filtering.

Optionally, the image combiner is configured to combine the first image signals and the second image signals based on noise-dependent weighting.

Optionally, the image combiner is configured to combine the first image signals and the second image signals in image domain based on noise reduction.

Optionally, the image combiner is configured to apply a first weight factor for the first image signals, and a second weight factor for the second image signals.

Optionally, the first weight factor is between 0.1 and 0.4.

Optionally, the first weight factor is 0.15.

Optionally, the first weight factor has a first value below 0.2 for a first frequency or first frequency range, and a second value above 0.2 for a second frequency higher than the first frequency or for a second frequency range higher than the first frequency range.

Optionally, the image combiner is configured to combine the first image signals and the second image signals based on modulation transfer function (MTF).

Optionally, the image combiner is configured to combine the first image signals and the second image signals based on noise power spectrum (NPS).

Optionally, the image combiner is configured to combine the first image signals and the second image signals based on detective quantum efficiency (DQE).

Optionally, the first scintillator layer is GOS-based.

Optionally, the second scintillator layer is glass-based.

Optionally, the first scintillator layer is thinner than the second scintillator layer.

Optionally, the first scintillator layer and the second scintillator layer are stacked.

Optionally, the imaging apparatus further includes a third scintillator layer, wherein the first scintillator layer, the second scintillator layer, and the third scintillator layer are stacked.

Optionally, the imaging apparatus further includes a fourth scintillator layer, wherein the first scintillator layer, the second scintillator layer, the third scintillator layer are stacked, and the fourth scintillator layer are stacked.

Optionally, the image combiner is configured to combine a third image signals associated with the third scintillator layer with the first image signals and the second image signals Optionally, the imaging apparatus is configured to provide a detective quantum efficiency of 5% or higher.

Optionally, the imaging apparatus is configured to provide a detective quantum efficiency of 6.5% or higher.

Some exemplary imaging methods include: obtaining first image signals generated by a first scintillator layer, the first image signals having a first quantum efficiency and a first spatial resolution; obtaining second image signals generated by a second scintillator layer, the second image signals having a second quantum efficiency and a second spatial resolution, wherein the first quantum efficiency is lower than the second quantum efficiency, but the first spatial resolution is higher than the second spatial resolution; and electronically processing the first image signals and the second images by an image combiner to combine the first image signals and the second image signals forming a combined image.

Some exemplary embodiments include a medium storing a set of instructions, an execution of which causes an imaging method to be performed, the imaging method comprising: obtaining first image signals generated by a first scintillator layer, the first image signals having a first quantum efficiency and a first spatial resolution; obtaining second image signals generated by a second scintillator layer, the second image signals having a second quantum efficiency and a second spatial resolution, wherein the first quantum efficiency is lower than the second quantum efficiency, but the first spatial resolution is higher than the second spatial resolution; and electronically processing the first image signals and the second images by an image combiner to combine the first image signals and the second image signals forming a combined image.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
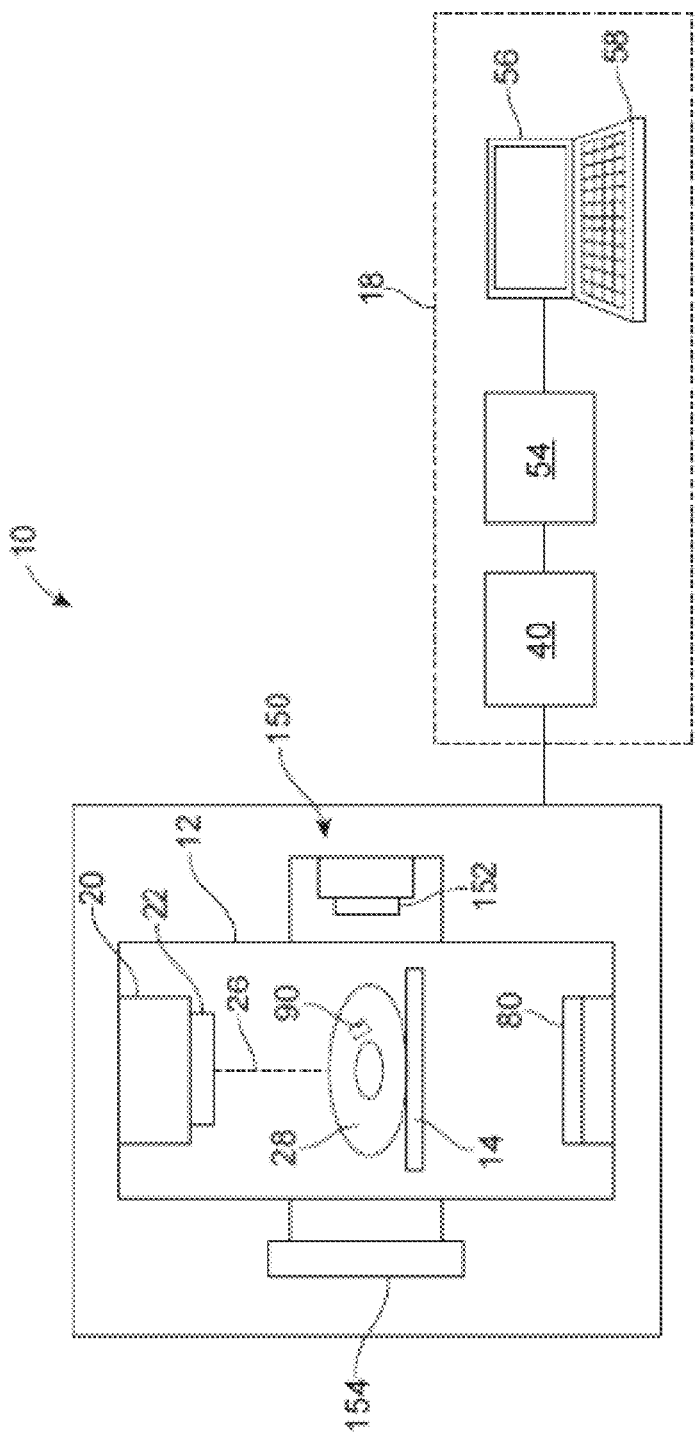
FIG. 1 illustrates a radiation system having an imaging apparatus in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation system 10. The system 10 is a treatment system that includes a gantry 12, a patient support 14 for supporting a patient 28, and a control system 18 for controlling an operation of the gantry 12. The gantry 12 is in a form of an arm, but in other embodiments, the gantry 12 may have other forms (such as a ring form, etc.). The system 10 also includes a radiation source 20 that projects a beam 26 of radiation towards a patient 28 while the patient 28 is supported on support 14, and a collimator system 22 for controlling a delivery of the radiation beam 26. The collimator 22 may be configured to adjust a cross sectional shape of the beam 26. The radiation source 20 can be configured to generate a cone beam, a fan beam, or other types of radiation beams in different embodiments.

As shown in the figure, the system 10 also includes an imager 80, located at an operative position relative to the source 20 (e.g., under the support 14). In the illustrated embodiments, the radiation source 20 is a treatment radiation source for providing treatment energy. In such cases, the treatment energy may be used by the imager 80 to obtain images. In order to obtain imaging using treatment energies, the imager 80 is configured to generate images in response to radiation having treatment energies (e.g., MV imager). In other embodiments, in addition to being a treatment radiation source, the radiation source 20 can also be a diagnostic radiation source for providing diagnostic (imaging) energy for imaging purpose. In further embodiments, the system 10 may include the radiation source 20 for providing treatment energy, and one or more other radiation sources for providing diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. Also, in some embodiments, a treatment energy may be 6 MV or higher (e.g., 25 MV). In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In other embodiments, the radiation source 20 may be configured to generate radiation at other energy ranges.

In the illustrated embodiments, the control system 18 includes a processing unit 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processing unit 54. In some cases, the control 40 may also control the collimator system 22 and the position of the patient support 14. In addition, in some embodiments, the control 40 may be configured to control an operation of the imager 80. Although the control 40 is shown as a separate component from the gantry 12 and the processor 54, in alternative embodiments, the control 40 can be a part of the gantry 12 or the processing unit 54.

In some embodiments, the system 10 may be a treatment system configured to deliver treatment radiation beam towards the patient 28 at different gantry angles. During a treatment procedure, the source 20 rotates around the patient 28 and delivers treatment radiation beam from different gantry angles towards the patient 28. While the source 20 is at different gantry angles, the collimator 22 is operated to change the shape of the beam to correspond with a shape of the target tissue structure. For example, the collimator 22 may be operated so that the shape of the beam is similar to a cross sectional shape of the target tissue structure. In another example, the collimator 22 may be operated so that different portions of the target tissue structure receive different amount of radiation (as in an IMRT procedure).

In the illustrated embodiments, the system 10 also includes an imaging device 150 having an imaging source 152 and an imager 154. The imaging device 150 is configured to obtain one or more images of an internal part of the patient 28. The image(s) obtained by the imaging device 150 may be used to setup the patient 28, monitor a position of the patient 28, track a target within the patient 28, or any combination of the foregoing. In some cases, the imaging device 150 may be configured to obtain images of an internal fiducial 90 of the patient 28. The internal fiducial 90 may be an internal structure inside the patient 28. In some embodiments, the internal structure may move in correspondence (e.g., in sync) with a target of the patient 28 that is desired to be treated. In such cases, the internal structure may be used as a surrogate for determining a position and/or movement of the target during treatment of the patient 28, and motion management based on the surrogate may be employed in some cases. Thus, the internal fiducial 90 may be imaged by the imaging device 150 (and/or by the radiation source 20 and imager 80) that functions as a position monitoring system during a treatment of the patient 28. By means of non-limiting examples, the internal fiducial 90 may be an anatomical surrogate, such as bony structure, a vessel, a natural calcification, or any other items in a body. As discussed, the imaging device 150 and/or the imager 80 may also be used for target tracking and/or patient positioning. In some embodiments, the control 40 may be configured to control an operation of the imaging device 150. For example, the control 40 may provide one or more control signals to activate the imaging source 152, and/or to operate a readout and control circuit in the imager 154.

In some embodiments, the imaging device 150 may be an x-ray device. In such cases, the imaging source 152 comprises a radiation source. In other embodiments, the imaging device 150 may have other configurations, and may be configured to generate images using other imaging techniques. For example, in other embodiments, the imaging device 150 may be an ultrasound imaging device, a MRI device, a tomosynthesis imaging device, or any of other types of imaging devices. Also, in the above embodiments, the imaging device 150 is illustrated as being integrated with the treatment machine. In other embodiments, the imaging device 150 may be a separate device that is separate from the treatment machine. In addition, in some embodiments, the imaging device 150 may be a room-based imaging system or a couch-based imaging system. In either case, the imaging device 150 may provide any form of imaging, such as x-ray imaging, ultrasound imaging, MRI, etc. Furthermore, in other embodiments, the imaging device 150 may provide in-line imaging in the sense that it may be configured to acquire images along the same direction as the treatment beam. For example, a dual-energy source (integrating the treatment source 20 and the imaging source 152) may be provided to provide imaging energy for generating an image, and to provide treatment energy to treat a patient along the same direction. In such cases, the imager 154 may replace the imager 80, or may be integrated with the imager 80 to form a hybrid-imager, which is configured to provide kV and MV imaging. In still further embodiments, the imaging device 150 and/or the imaging device 80 may be configured to provide dual energy imaging and any form of energy-resolved imaging to increase contrast in x-ray images. For example, a first part of an image may be generated using a first energy, and a second part (e.g., a more relevant part that includes a target) of the same image may be generated using a second energy that is higher than the first energy. As a result, the second part of the image may have higher contrast compared to the first part. However, the overall dose involved in generating the whole image may be reduced compared to the situation in which the entire image is generated using the second energy.

Figure 2:
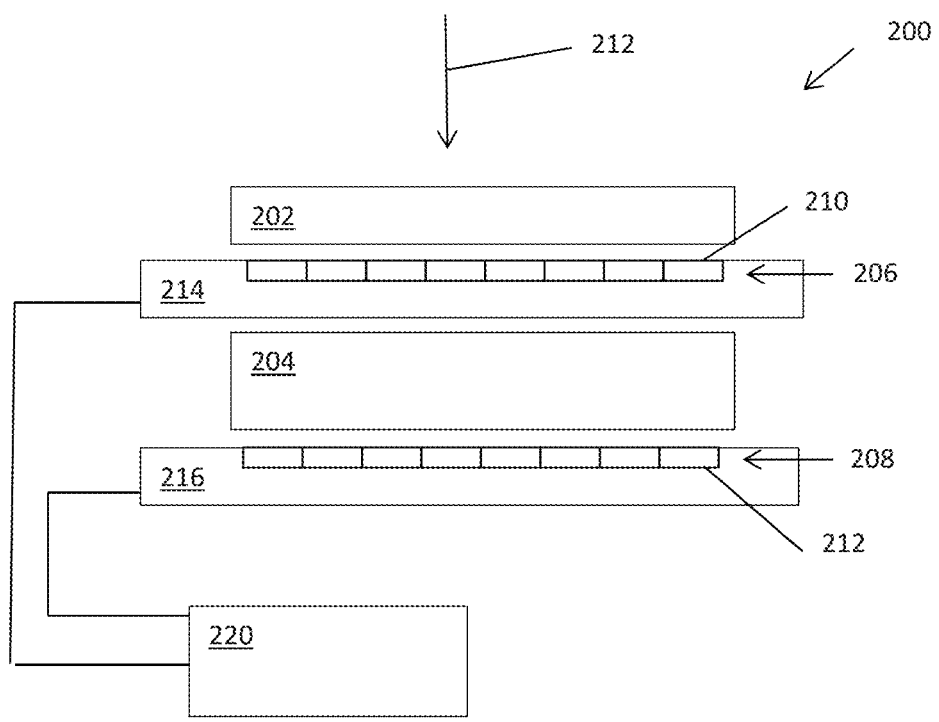
FIG. 2 illustrates an imaging apparatus in accordance with some embodiments.

FIG. 2 illustrates an imaging apparatus 200 in accordance with some embodiments. The imaging apparatus 200 may implement as the imager 80 of FIG. 1 in some embodiments. The imaging apparatus 200 includes a first scintillator layer 202, a second scintillator layer 204, a first photodiode layer 206, a second photodiode layer 208, and an image combiner 220.

The first scintillator layer 202 is configured to receive radiation 212 and generate first photons in response to the radiation 212. The radiation 212 may be treatment radiation having an energy level that is sufficient for treatment of a patient. The first photodiode layer 206 includes first photodiode elements 210 that are configured to convert first photons into first electrical signals for readout by a readout circuit. The first electrical signals may be considered as first image signals forming a first image. The first scintillator layer 202 may be pixelated or non-pixelated.

The second scintillator layer 204 is configured to receive radiation after it has passed through the first scintillator layer 202, and to generate second photons in response to the radiation. The second photodiode layer 208 includes second photodiode elements 212 that are configured to convert second photons into second electrical signals for readout by the readout circuit. The second electrical signals may be considered as second image signals forming a first image. The second scintillator layer 204 may be pixelated or non-pixelated.

In some embodiments, each photodiode element 210/212 may include one or more amorphous silicon (a:Si) detector. Also, in some embodiments, the photodiode element 210/212 may be implemented using a photodiode. In this specification, the term "photodiode" refers to one or more electrical circuit element(s) on a detector pixel that are associated with converting photon energy into electrical signals. This can include, but is not limited to, photodiode (s), switching transistor(s), amplification transistor(s), direct conversion element, indirect conversion elements, photon counting elements, or a combination thereof. In some embodiments, signal from each photodiode element 210/212 forms a pixel in an image. In other embodiments, a binning circuit is optionally provided to combine the signals from two or more photodiode elements to form each pixel in the image. For example, the binning circuit of the imager 200 may be configured to provide 2×2 binning, 3×3 binning, 4×4 binning, 1×2 binning, 1×4 binning or binning of other number of pixels. The binning circuit may be implemented as a part of the readout circuit in some embodiments. In some embodiments, the readout circuit may be communicatively connected to the control 40, or another separate control, for controlling an operation of the readout circuit. Also, in some embodiments, the readout circuit may be included as a part of the image combiner 220, or may be communicatively coupled to the image combiner 220.

As shown in FIG. 2, the image elements 210 is secured to a first substrate 214, and the image elements 212 are secured to the second substrate 216. In the illustrated embodiments, the image elements 210 of the first photodiode layer 206 are closer to a first side (e.g., a top side) of the substrate 214 than to a second side (e.g., a bottom side) of the substrate 214. Also, the image elements 212 of the first photodiode layer 208 are closer to a first side (e.g., a top side) of the substrate 216 than to a second side (e.g., a bottom side) of the substrate 216. In other embodiments, the image elements 210 of the first photodiode layer 206 are closer to the second side (e.g., the bottom side) of the substrate 214 than to the first side (e.g., the top side) of the substrate 214. Also, in other embodiments, the image elements 212 of the first photodiode layer 208 are closer to the second side (e.g., the bottom side) of the substrate 216 than to the first side (e.g., the top side) of the substrate 216. The substrates 214, 216 may be made from glass, plastic, or other materials.

In some embodiments, the first scintillator layer 202 may be GOS-based. For example, the first scintillator layer 202 may be a Gadolinium oxysulfide scintillator layer. Also, the second scintillator layer 204 may be glass-based. For example, the scintillator layer 204 may be a LKH5 scintillator. Although LKH5 scintillator is mentioned here as an example, it should be noted that the scintillator layer 204 may be any glass high density scintillator. Also, in other embodiments, the scintillator layer 204 may not be glass-based. Instead, in other embodiments, the scintillator layer 204 may be non-glass-based. The scintillator layer 204 may be made from any material as long as it provides high absorption of x-rays (compared to the scintillator layer 202), and good conversion efficiency (compared to the scintillator layer 202). Such a scintillator may be thicker than the scintillator layer 202, and may produce some blurring in the final image.

As shown in FIG. 1, the first scintillator layer 202 is thinner than the second scintillator layer 204, and the first scintillator layer 202 and the second scintillator layer 204 are arranged relative with each other in a stacked configuration. For example, in some embodiments, the first scintillator layer 202 may have a thickness that is between 200 um and 1 mm (e.g., 436 um), and the second scintillator layer 202 may have a thickness that is between 1 mm and 5 mm (e.g., 3 mm). In other embodiments, the first and second scintillator layers 202, 204 may have other thicknesses. In the illustrated embodiments, the first scintillator layer 202 is above the second scintillator layer 204 so that the first scintillator layer 202 receives the radiation 212 before the second scintillator layer 204. In other embodiments, the second scintillator layer 204 may be arranged above the first scintillator layer 202 so that the second scintillator layer 204 receives the radiation 212 before the first scintillator layer 202.

The image combiner 220 is configured to obtain the first image signals and the second image signals, and combine them to form a combined image. Because the first and second photodiode layers 206, 208 separately receive photos from the respective scintillator layers 202, 204, and create separate first and second image signals that correspond with the respective scintillator layers 202, 204, the image combiner 220 can separate process (e.g., by apply weight factors, filtering, etc.) the first and second image signals before combining them. In some embodiments, the image combiner 220 may be configured to combine the first image signals and the second image signals in a way that increase signal-to-noise ratio while reducing spatial resolution loss. Also, in some embodiments, the image combiner 220 may be configured to combine the first image signals and the second image signals based on frequency-dependent weighting. Alternatively, or additionally, the image combiner 220 may be configured to combine the first image signals and the second image signals based on frequency-dependent filtering. Alternatively, or additionally, the image combiner 220 may be configured to combine the first image signals and the second image signals based on noise-dependent weighting.

In some embodiments, the image combiner 220 is configured to apply a first weight factor for the first image signals, and a second weight factor for the second image signals. For example, the first weight factor may be between 0.1 and 0.4, and more preferably between 0.12 and 0.2, (e.g., 0.15). The second weight factor may be a value that is equal to 1 minus the first weight factor. Also, in some embodiments, the first weight factor may have a first value below a threshold for a first frequency or first frequency range, and a second value above the threshold for a second frequency higher than the first frequency, or for a second frequency range higher than the first frequency range. The threshold may be between 0.1 and 0.3, and more preferably between 0.15 and 0.25, such as 0.2).

In some embodiments, the image combiner 220 may be configured to combine the first image signals and the second image signals based on modulation transfer function (MTF), noise power spectrum (NPS), detective quantum efficiency (DQE), or any combination of the foregoing. As discussed, the image combiner 220 may be configured to combine the first image signals and the second image signals based on frequency-dependent weighting and/or filtering. By means of non-limiting examples, the frequency-dependent weighting and/or filtering may be based on MTF, NPS, DQE, or any combination of the foregoing.

Also, in some embodiments, the image combiner 220 may be configured to combine the first image signals and the second image signals based on noise-dependent weighting factors, which can be estimated either by calculating the first-order statistics of noises in both images or by iteratively enforcing a regularization constraint such as the total variation of output image. Furthermore, in some embodiments, the image combiner 220 may be configured to combine the first image signals and the second image signals based on weighting factors, wherein the weighting factors may be frequency-dependent, noise-dependent, or a combination of the foregoing. Also, in some embodiments, the image combiner 220 is configured to combine the first image signals and the second image signals to maximize DQE (or SNR) for the combined image. In addition, in some embodiments, the image combiner 220 may be configured to combine the first image signals and the second image signals based on weighting that account for imaging task (e.g., task transfer function), and/or observer model (e.g., eye filter, human observer, hoteling observer, etc.).

In some embodiments, the image combiner 220 may be configured to combine the first image signals contributed by the first scintillator layer 202, and the second image signals contributed by the second scintillator layer 204, in frequency domain. In other embodiments, the image combiner 220 may be configured to combine the first image signals and the second image signals in image domain. For example, the image combiner 220 may be configured to combine the first image signals and the second image signals in image domain based on noise reduction. In further embodiments, the image combiner 220 may be configured to combine the first image signals and the second image signals in both frequency and image domains. For example, the image combiner 220 may be configured to perform image fusion in both the frequency domain and image domain one after another (e.g., in frequency domain first and then followed by image domain, or vice versa), or simultaneously. Also, in some embodiments, the image combiner 220 may perform image fusion in the frequency domain by application of various frequency filters that depend on MTF, NPS, DQE, or any combination of the foregoing. Alternatively, or additionally, the image combiner 220 may perform image fusion in the image domain based on a direct or an iterative technique designed to reduce noise in the fused image and preserve spatial resolution.

In some embodiments, before combining the first image signals and the second image signals, the image combiner 220 may be configured to (1) seal off bad pixels and correct images with Dark Field (DF) and Flat Field (FF) datasets, (2) remove scatter from images (e.g., with polynomial detrending), (3) normalize images to a common background, (4) register the images with respect to each other, or any combination of the foregoing. In some cases, to seal off bad pixels (e.g., due to photodiode being dead or underperformed), the image combiner 220 may correct bad pixels such that new values of the bad pixels will be similar to neighboring pixels. In one implementation, interpolation between the neighboring pixels may be performed to determine new values for the bad pixels. In other embodiments, one or more of the above features may be performed by a module that is coupled upstream with respect to the image combiner 220.

In some embodiments, the imaging apparatus 200 is configured to provide a detective quantum efficiency (DQE) of 5% or higher, or more preferably 6.5% or higher.

Although the imaging apparatus 200 has been described as having two scintillator layers 202, 204, and two corresponding photodiode layers 206, 208, in other embodiments, the imaging apparatus 200 may have more than two scintillator layers, and more than two photodiode layers. For example, in some embodiments, the imaging apparatus 200 may further include a third scintillator layer and a corresponding third photodiode layer (for generating third image signals in response to photons from the third scintillator layer). In such cases, the first scintillator layer 202, the second scintillator layer 204, and the third scintillator layer may be stacked. For example, the third scintillator layer and the third photodiode layer may be placed below the second substrate 216. Alternatively, the third scintillator layer and the third photodiode layer may be placed between the first substrate 214 and the second scintillator layer 204. In other embodiments, the third scintillator layer and the third photodiode layer may be placed above the first scintillator layer 202.

In further embodiments, the imaging apparatus 200 may further include a fourth scintillator layer and a corresponding fourth photodiode layer (for generating fourth image signals in response to photons from the fourth scintillator layer), wherein the first scintillator layer 202, the second scintillator layer 204, the third scintillator layer are stacked, and the fourth scintillator layer are stacked.

Figure 3:
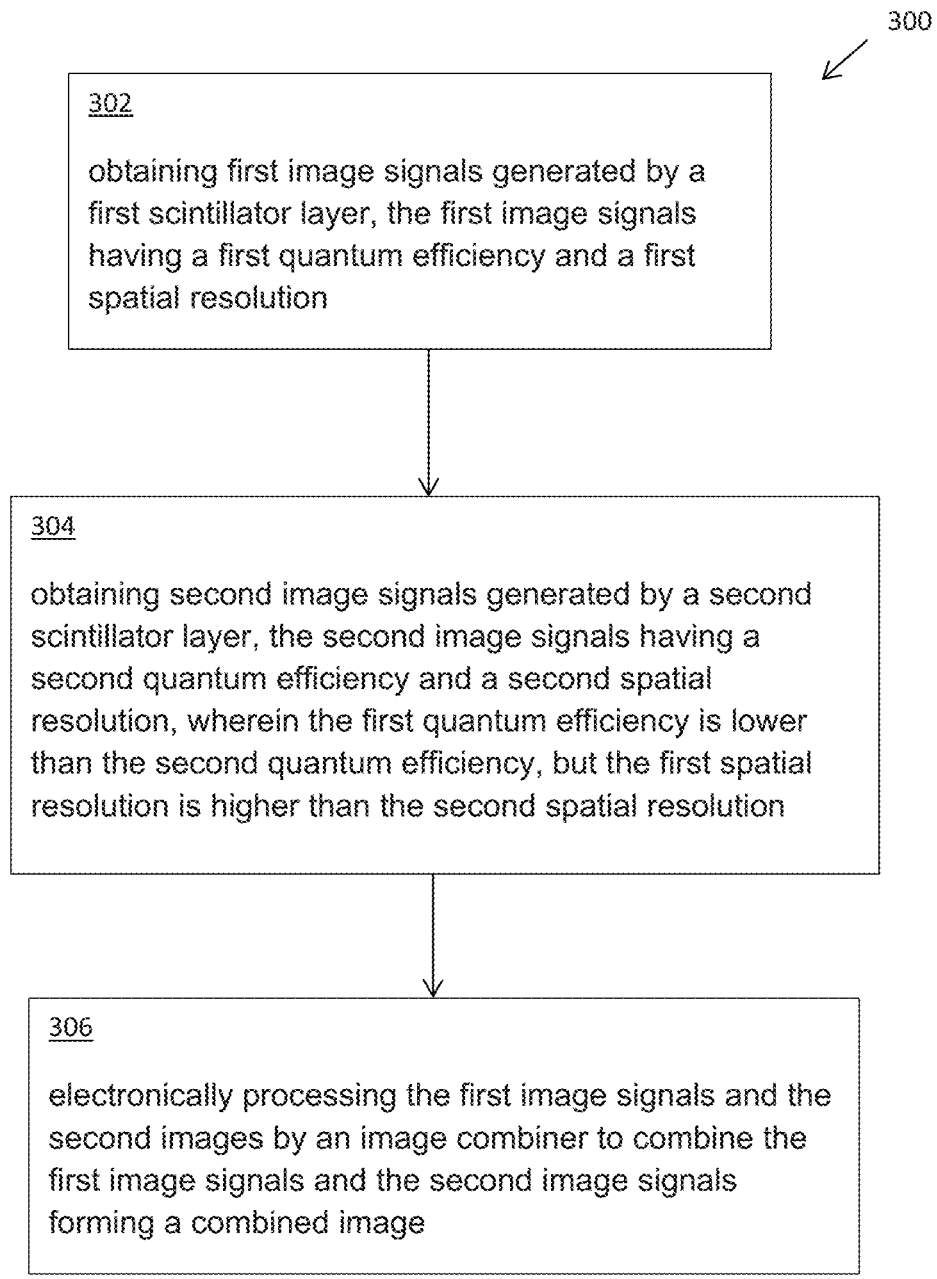
FIG. 3 illustrates a method of combining image signals in accordance with some embodiments.

FIG. 3 illustrates a method 300 of combining image signals. In some embodiments, the method 300 may be performed by the imaging apparatus 200 of FIG. 2. The method 300 includes obtaining first image signals generated by a first scintillator layer, the first image signals having a first quantum efficiency and a first spatial resolution (item 302). The method 300 also includes obtaining second image signals generated by a second scintillator layer (item 304). In the illustrated example, the second image signals have a second quantum efficiency and a second spatial resolution, wherein the first quantum efficiency is lower than the second quantum efficiency, but the first spatial resolution is higher than the second spatial resolution. The method 300 further includes electronically processing the first image signals and the second images by an image combiner to combine the first image signals and the second image signals forming a combined image (item 306).

In some embodiments, in item 306, the first image signals and the second image signals are combined in a way that increase signal-to-noise ratio while reducing spatial resolution loss.

In some embodiments, in item 306, the first image signals and the second image signals are combined based on frequency-dependent weighting.

In some embodiments, in item 306, the first image signals and the second image signals are combined based on frequency-dependent filtering.

In some embodiments, in item 306, the first image signals and the second image signals are combined based on noise-dependent weighting.

In some embodiments, in item 306, the first image signals and the second image signals are combined in image domain based on noise reduction.

In some embodiments, in item 306, an image combiner applies a first weight factor for the first image signals, and a second weight factor for the second image signals.

In some embodiments, in the method 300, the first weight factor is between 0.1 and 0.4. In some embodiments, the first weight factor is 0.15.

In some embodiments, in the method 300, the first weight factor has a first value below 0.2 for a first frequency or first frequency range, and a second value above 0.2 for a second frequency higher than the first frequency or for a second frequency range higher than the first frequency range.

In some embodiments, in item 306, the first image signals and the second image signals are combined based on MTF.

In some embodiments, in item 306, the first image signals and the second image signals are combined based on NPS.

In some embodiments, in item 306, the first image signals and the second image signals are combined based on DQE.

In some embodiments, in the method 300, the first scintillator layer is GOS-based.

In some embodiments, in the method 300, the second scintillator layer is glass-based.

In some embodiments, in the method 300, the first scintillator layer is thinner than the second scintillator layer.

In some embodiments, in the method 300, the first scintillator layer and the second scintillator layer are stacked.

In some embodiments, the method 300 provides a detective quantum efficiency of 5% or higher, or more preferably 6.5% or higher.

Figure 4:
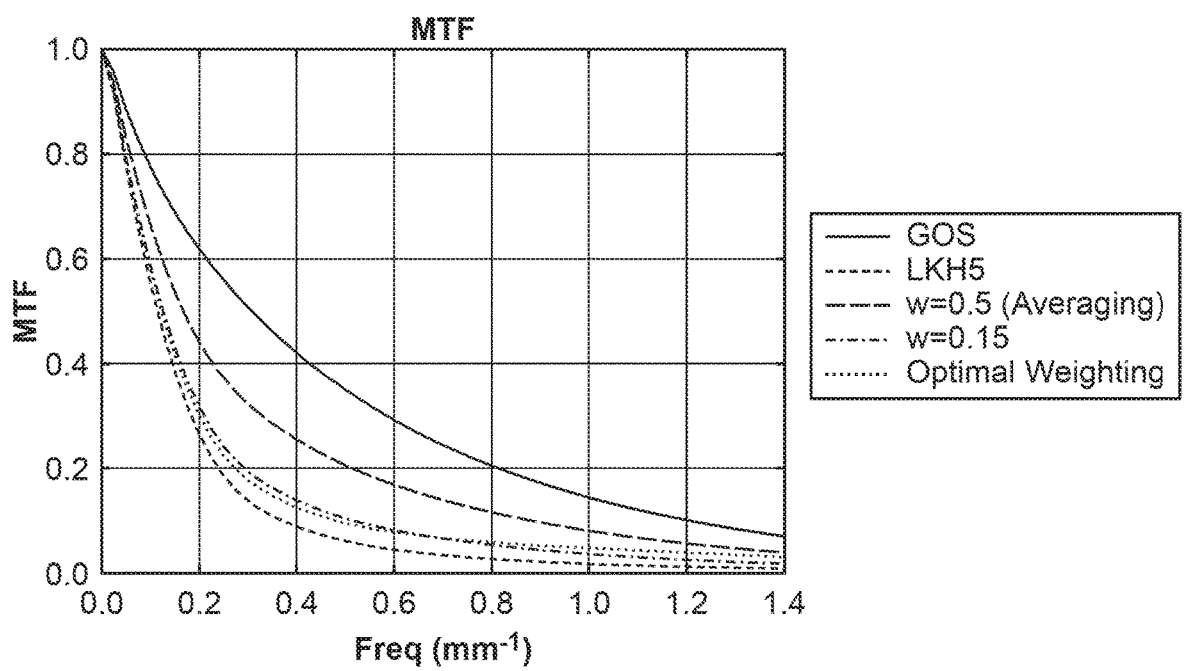
FIG. 4 illustrates the relationship between MTF values and frequency values.
Figure 5:
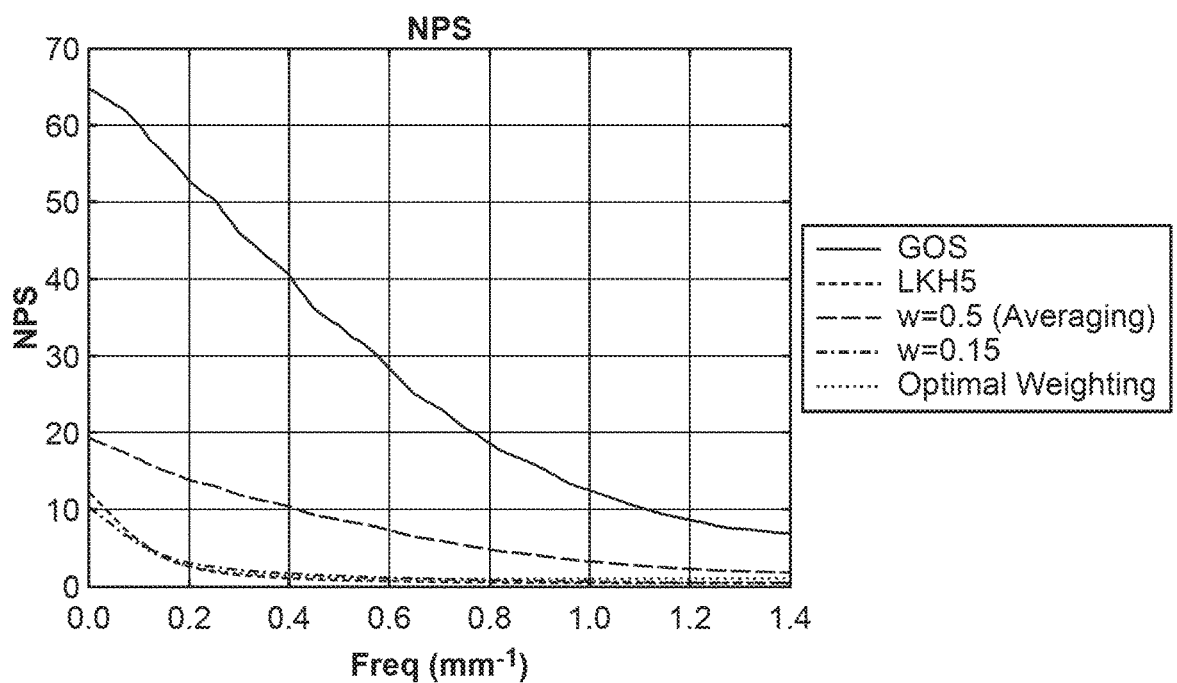
FIG. 5 illustrates the relationship between MPS values and frequency values.
Figure 6:
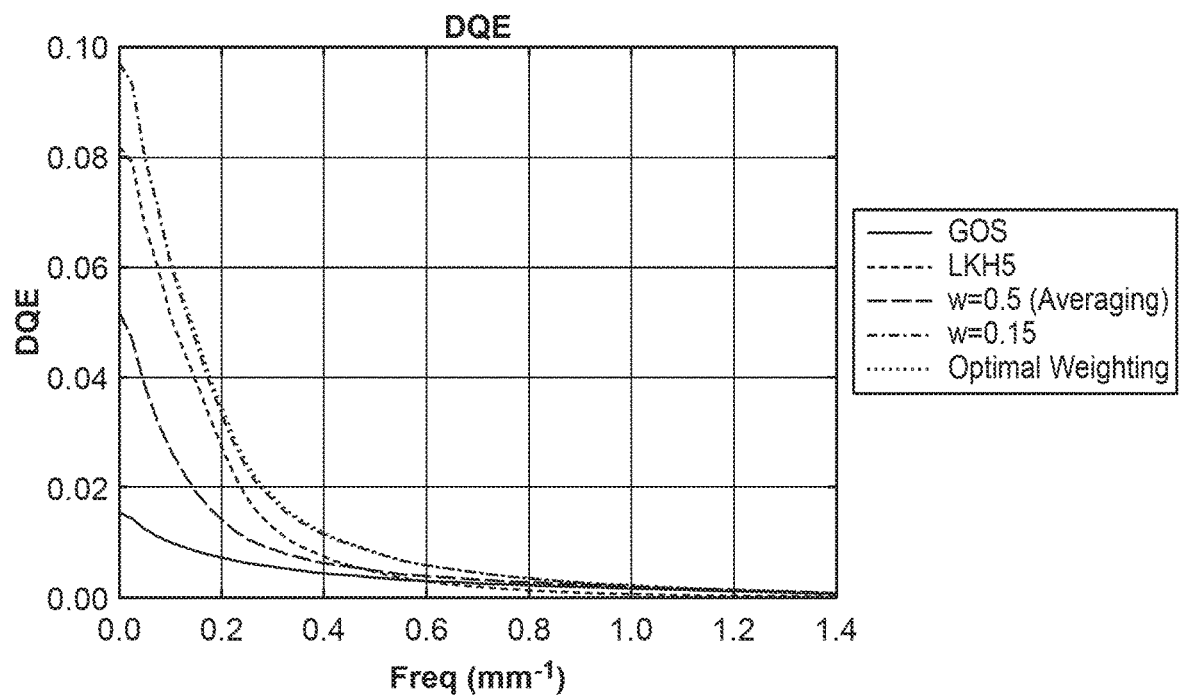
FIG. 6 illustrates the relationship between DQE values and frequency values.

As discussed, in some embodiments, the combining of the first image signals and the second image signals may be performed based on MTF, NPS, DQE, or any combination of the foregoing. FIGS. 4-6 illustrate imaging characteristics of a GOS-based scintillator (which is an example of the first scintillator layer 202), and imaging characteristics of a glass-based scintillator (which is an example of the second scintillator layer), particularly showing MTF, NPS, and DQE as functions of, or in relation with, frequencies. In particular, FIG. 4 illustrates relationship between MTF values and frequency values. FIG. 5 illustrates relationship between MPS values and frequency values. FIG. 6 illustrates relationship between DQE values and frequency values. As shown in FIG. 4, the MTF value associated with the first scintillator layer 202 (e.g., GOS-based scintillator) is generally higher than the MTF value associated with the second scintillator layer 204 (e.g., glass-based scintillator). This is because due to the grainy structure of GOS image, the MTF characteristics are very good, i.e., it provides "high" spatial resolution compared to the glass-based image (e.g., LKH5 image). The glass-based image, on the other hand, suffers from light blurring and therefore yields a "low" spatial resolution. Also, as shown in FIG. 6, the DQE value associated with the first scintillator layer 202 (e.g., GOS-based scintillator) is lower than the DQE value associated with the second scintillator layer 204 (e.g., glass-based scintillator). The above information may be utilized by the image combiner 220 in combining the first image signals and the second image signal, such that the resulting combined image will have high resolution features (e.g., higher than that of the second image signals) carried over from the first images signals, and high DQE (or SNR) (e.g., higher than that of the first image signals) carried over from the second image signals. In one embodiment such image combination can be performed using frequency-dependent filtration or weighting where the weighting factor (w) is determined by MTF and NPS characteristic curves. In this case MTF determines frequency-dependent "resolution" of the image while NPS curve suggests amount of noise generated in the system and, furthermore, identifies detective quantum efficiency. For example, low efficiency high resolution of GOS-based scintillator and high efficiency and low resolution of glass-based scintillator suggest that during image fusion it would be preferable to use high frequency content of GOS-based scintillator image and low frequency content of glass-based scintillator image. It means that GOS-based scintillator image should have a lower weight at low frequency region and higher weight at high frequency region, while the remaining "1-w" weight would be applied to glass-based scintillator image, respectively. In some embodiments, the image combiner 220 is configured to combine the first image signals and the second image signals to maximize DQE (or SNR) for the combined image, while preserving spatial resolution. In one implementation, first image (first image signals) and second image (second image signals) may be normalized (by the image combiner 220 or by a normalization unit coupled upstream to the image combiner 220) prior to being combined based on the following:

$$GOS: DQE_1(f) = \frac{MTF_1^2(f)}{NPS_1(f)}$$

$$\text{LKH5: } DQE_2(f) = \frac{MTF_2^2(f)}{NPS_2(f)}$$

Then the image combiner 220 may perform frequency-dependent linear combination of the first and second images based on the following:

$$Im_3(f)=w(f)\cdot Im_1(f)+(1-w(f))\cdot Im_2(f)$$

$$MTF_3(f)=w(f)MTF_1(f)+(1-w(f))\cdot MTF_2(f)$$

$$NPS_3(f)=w^2(f)NPS_1(f)+(1-w(f))^2 NPS_2(f)$$

The DQE of the combined image (DQE$_3$) may then be maximized by the image combiner 220 according to the following:

$$DQE_3(f): w(f) = \left[\frac{MTF_1/NPS_1}{MTF_1/NPS_1 + MTF_2/NPS_2}\right](f)$$

In other embodiments, the image combiner 220 may be configured to combine the first and second images by maximizing SNR of the resulting image based on Rose noise model. According to the Rose noise model, the SNR may be defined as a product of a contrast-to-noise ratio (CNR) and the square root of the number of pixels N in the area of interest, as follows:

$$SNR=CNR\sqrt{N}.$$

The CNR may be expressed in terms of signal ($I_s$) and background ($I_b$) intensities and their standard deviations $\sigma_s$ and $\sigma_b$:

$$CNR=(I_s-I_b)/\sqrt{\sigma_s^2+\sigma_b^2}.$$

In some cases, a figure-of-merit (FOM) may be utilized to optimize the SNR with respect to the integral dose D delivered to the patient, wherein FOM may be defined as:

$$FOM=SNR/\sqrt{D}.$$

Figure 7:
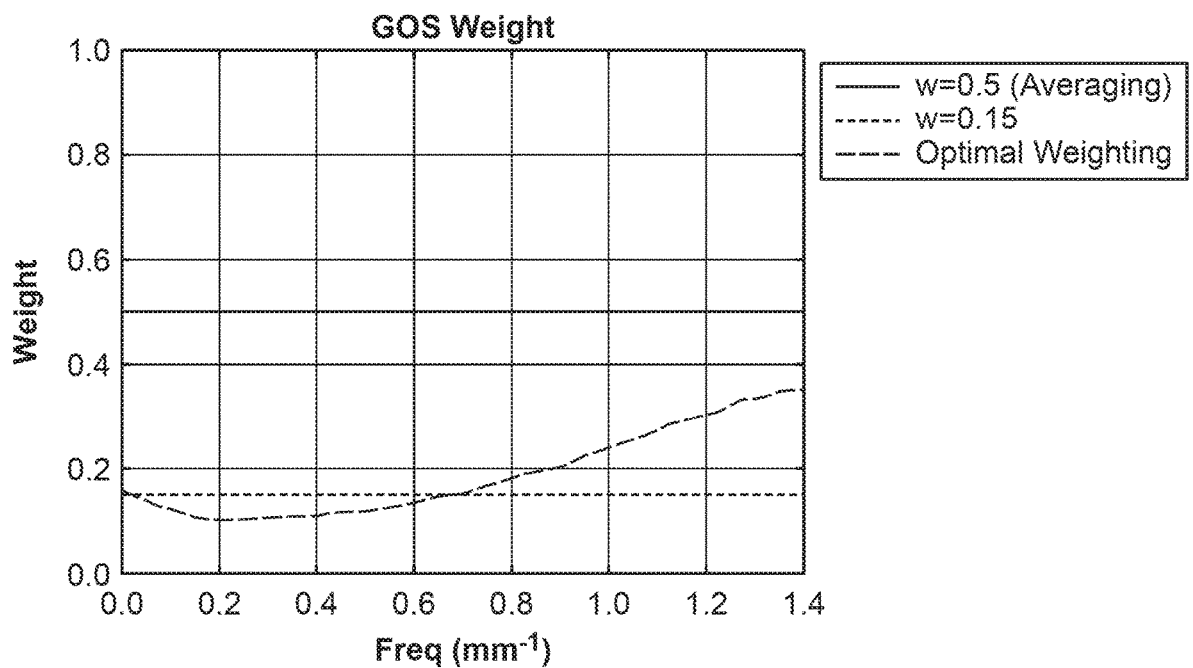
FIG. 7 illustrates weight factor as function of frequency.

FIG. 7 illustrates weight factor as function of frequency for the imaging apparatus 200. As shown in the figure, the optimal weighting (weight factor) for the first image signals has different values depending on the frequency values. If a weight factor of 0.15 is applied for the first image signals contributed by the first scintillator layer 202, it provides a good approximation to the optimal values for a majority of the applicable frequency range (e.g., from 0 to 1.4 mm^-1). Accordingly, in some embodiments, the image combiner 220 may be configured to apply a first weight factor of 0.15 for the first image signals contributed by the first scintillator layer 202, and a second weight factor of 0.85 (=1−0.15) for the second image signals contributed by the second scintillator layer 204, regardless of the frequency values. In other embodiments, the image combiner 220 may be configured to apply a first weight factor that is between 0.1 and 0.4 for the first image signals, and a second weight factor that is 1 minus the first weight factor for the second image signals. Furthermore, in other embodiments, the image combiner 220 may be configured to apply a first weight factor having a first value for the first image signals for a first frequency range, and a first weight factor having a second value for the image signals for a second frequency range. In such cases, the image combiner 220 may also be configured to apply a second weight factor having a third value (that is equal to 1 minus the first value of the first weight factor) for the second image signals for the first frequency range, and a second weight factor having a fourth value (that is equal to 1 minus the second value of the first weight factor) for the second image signals for the second frequency range. In some embodiments, the first frequency range may be below a frequency threshold, and the second range may be above the frequency threshold.

Figure 8:
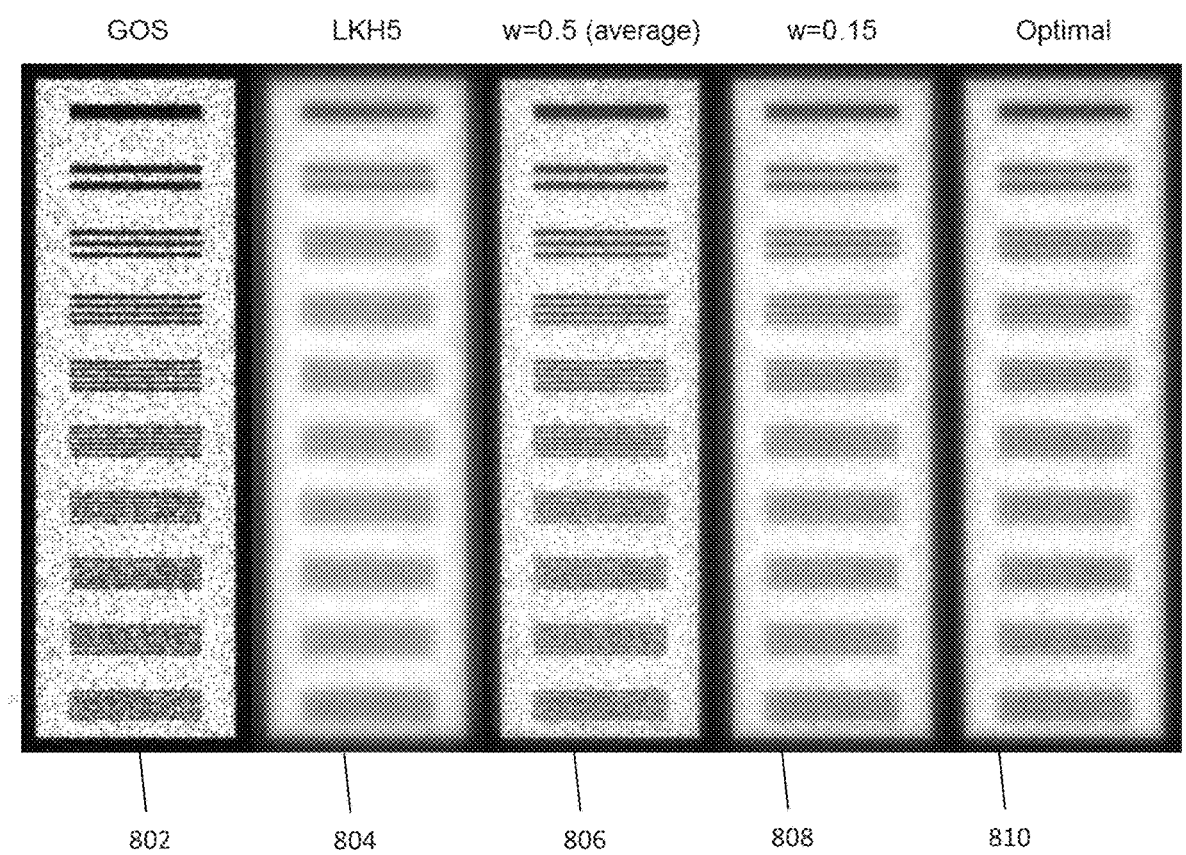
FIG. 8 illustrates results of image fusion.

FIG. 8 illustrates exemplary results of image fusion. The image 802 is based on image signals generated from a GOS-based scintillator (which is an example of the first scintillator layer 202). The image 804 is based on image signals generated from glass-based scintillator (which is an example of the second scintillator layer 204). As shown in the figure, the image 802 has a relatively higher resolution compared to the image 804, but the image 802 is generated with a relatively lower quantum efficiency compared to the image 804. Thus, the image 802 has a strong grainy noise structure and low SNR compared to the image 804. This is consistent with the MTF curves presented in FIG. 4. Namely, the GOS-based scintillator produces the MTF curve with slow-dropping tail in high frequency region. The MTF of the glass-based scintillator drops down much quicker than the GOS-based scintillator.

The image 806 is obtained from taking an average of the image 802 and the image 804, which is the same as applying a 0.5 weight factor to the image 802, applying a 0.5 weight factor to the image 804, and adding them. The image 808 is obtained by applying a 0.15 weight factor to the image 802, applying a 0.85 weight factor to the image 804, and combining them. The image 810 is obtained by determining optimal weighting through optimal balance of preserving spatial frequency (relating to MTF) and noise power reduction (NPS), applying the optimal weighting to the image 802 and the image 804, and combining them. As shown in the figure, the application of the 0.15 weight factor provides an image fusion result that is similar to that achieved through optimization. Thus, both 0.15 weight factor and optimal weighting provide images that retain high-DQE features of the second image (e.g., the glass-based image associated with the second scintillator layer 204) in the expense of spatial resolution, in that the MTF is lower than the 0.5 weight factor, but is higher than the second image alone.

Figure 9:
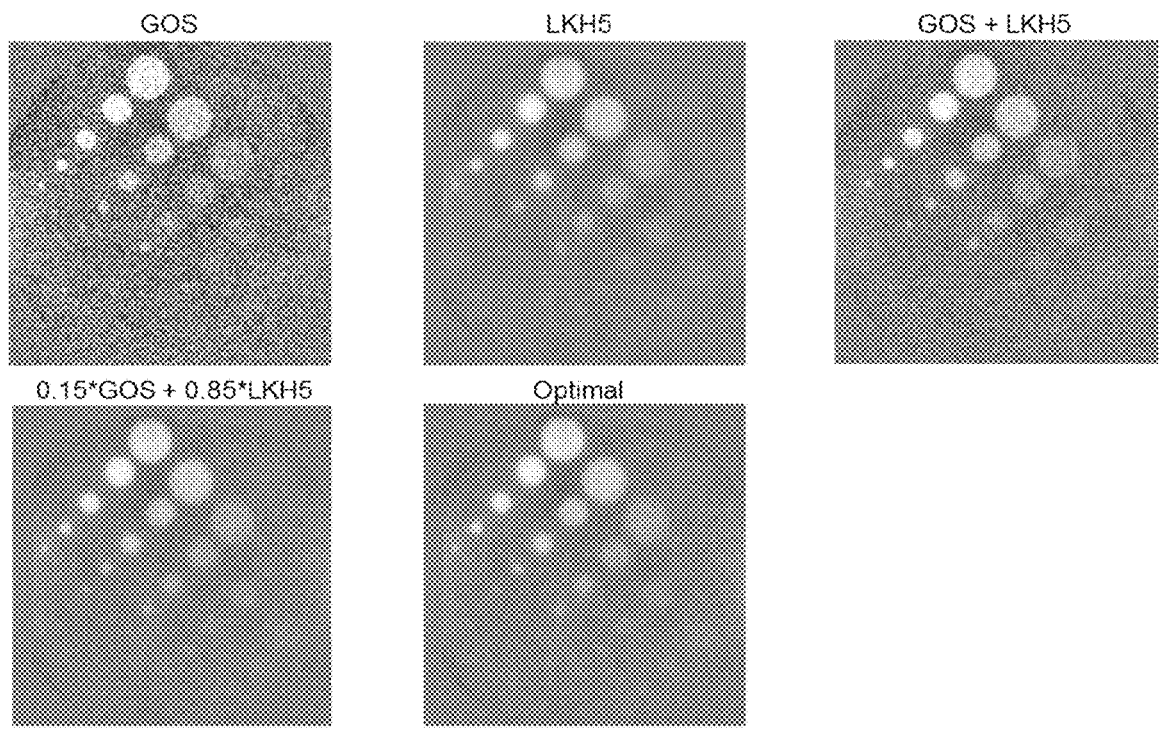
FIG. 9 illustrates image fusion performed using simulations.

FIG. 9 illustrates image fusion performed using simulation performed on phantom and MV beams. The GOS image is based on image signals generated from a GOS-based scintillator (which is an example of the first scintillator layer 202). The LKH5 image is based on image signals generated from LKH5 scintillator (which is an example of the second scintillator layer 204). As shown in the figure, the GOS image has a relatively higher resolution compared to the LKH5 image, but the GOS image is generated with a relatively lower quantum efficiency compared to the LKH5 image. Thus, the GOS image has a strong grainy noise structure and low SNR compared to the LKH5 image. The GOS+LKH5 image is obtained from taking an average of the GOS image and the LKH5 image, which is the same as applying a 0.5 weight factor to the GOS image, applying a 0.5 weight factor to the LKH5 image, and adding them. The "0.15*GOS+0.85*LKH5" image is obtained by applying a 0.15 weight factor to the GOS image, applying a 0.85 weight factor to the LKH5 image, and combining them. The optimal image is obtained by determining optimal weighting through optimal balance of preserving spatial frequency (relating to MTF) and noise power reduction (NPS), applying the optimal weighting to the GOS image and the LKH5 image, and combining them. As shown in the figure, the application of the 0.15 weight factor provides an image fusion result that is similar to that achieved through optimization. Thus, both 0.15 weight factor and optimal weighting provide images that retain high-DQE features of the second image (e.g., the LKH5 image associated with the second scintillator layer 204) in the expense of spatial resolution, in that the MTF is lower than the 0.5 weight factor, but is higher than the second image alone.

Figure 10:
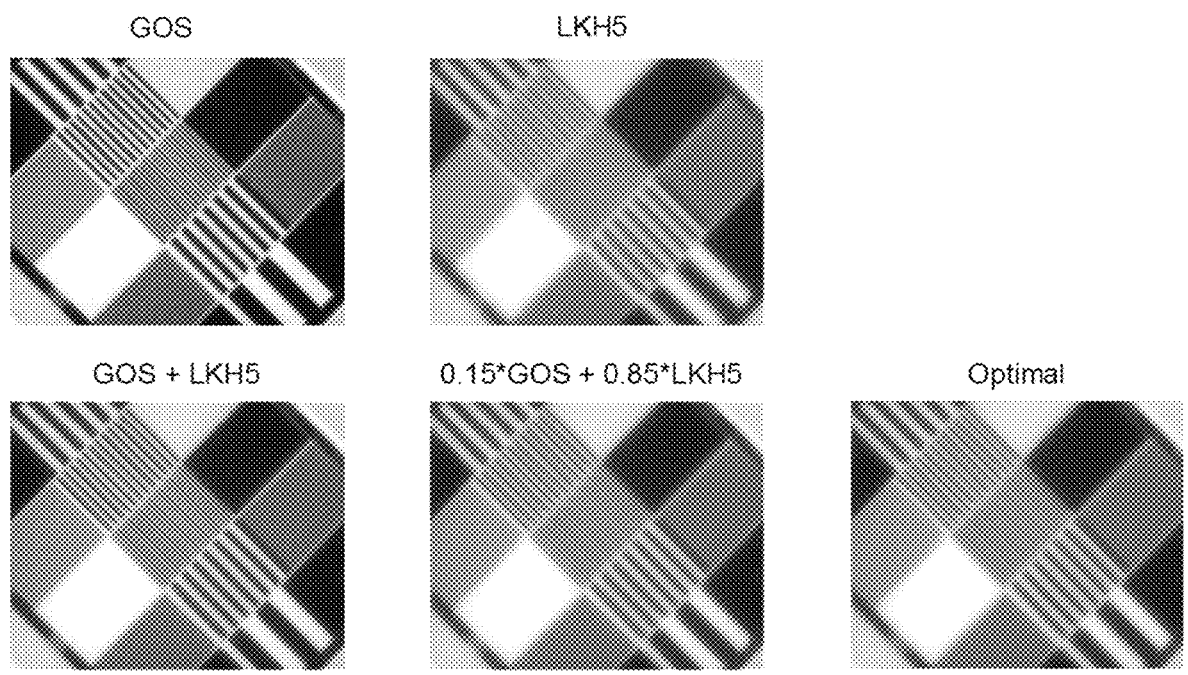
FIG. 10 illustrates image fusion performed using simulations.

FIG. 10 illustrates another image fusion performed using simulation performed on phantom and MV beams. The GOS image is based on image signals generated from a GOS-based scintillator (which is an example of the first scintillator layer 202). The LKH5 image is based on image signals generated from LKH5 scintillator (which is an example of the second scintillator layer 204). As shown in the figure, the GOS image has a relatively higher resolution compared to the LKH5 image, but the GOS image is generated with a relatively lower quantum efficiency compared to the LKH5 image. Thus, the GOS image has a strong grainy noise structure and low SNR compared to the LKH5 image. The GOS+LKH5 image is obtained from taking an average of the GOS image and the LKH5 image, which is the same as applying a 0.5 weight factor to the GOS image, applying a 0.5 weight factor to the LKH5 image, and adding them. The "0.15*GOS+0.85*LKH5" image is obtained by applying a 0.15 weight factor to the GOS image, applying a 0.85 weight factor to the LKH5 image, and combining them. The optimal image is obtained by determining optimal weighting through optimal balance of preserving spatial frequency (relating to MTF) and noise power reduction (NPS), applying the optimal weighting to the GOS image and the LKH5 image, and combining them. As shown in the figure, the application of the 0.15 weight factor provides an image fusion result that is similar to that achieved through optimization. Thus, both 0.15 weight factor and optimal weighting provide images that retain high-DQE features of the second image (e.g., the LKH5 image associated with the second scintillator layer 204) in the expense of spatial resolution, in that the MTF is lower than the 0.5 weight factor, but is higher than the second image alone.

In some embodiments, the combined image achieved using image fusion technique described herein provides better soft tissue visualization compared to if only thick glass-based scintillator layer is used. Also, in some embodiments, the combined image achieved using image fusion technique described herein allows for better detection of small (high frequency) features compared to if only thick glass-based scintillator layer is used (as in current EPID imagers). In further embodiments, the combined image achieved using image fusion technique described herein achieves noise reduction and edge enhancement that is better compared to current EPID imagers. In addition, in some embodiments, the image fusion technique described herein provides lower-dose MV imaging compared to current EPID imagers. In some embodiments, the image fusion technique described herein may be performed during a treatment procedure, e.g., for soft tissue visualization, patient positioning, etc.

In some embodiments, the first scintillator layer 202 and the second scintillator layer 204 may be configured to provide detective quantum efficiency (DQE) of at least 5%. One exemplary configuration providing such 5% DQE may utilize a 436 μm thick GOS-based scintillator and a 3 mm thick glass-based scintillator, wherein the GOS-based scintillator would yield about 1.8% DQE, and the glass-based scintillator would result in about 3.8% DQE. The thickness and efficiency of glass-based scintillator are not limited to numbers discussed, and can have higher or lower values in other embodiments. DQE is a measure of a combined effects of the signal (related to image contrast) and noise performance of an imaging system. In some cases, DQE may be expressed as a function of spatial frequency. In other embodiments, the DQE may be improved to achieve higher values, such as 6.5% or greater. For example, in other embodiments, the thickness of the first scintillator layer 202 and/or the thickness of the second scintillator layer may be increased. Also, in some embodiments, the imaging apparatus 200 may include additional scintillator layer(s), as discussed, for providing higher DQE.

In some embodiments, the first scintillator layer 202 and the second scintillator layer 204 provides a DQE that is higher than a single layer EPID (which may have only 1.8% DQE). Also, in some embodiments, the first scintillator layer 202 and the second scintillator layer 204 may be configured to provide a DQE that is higher than a four-layer design that has four layers of GOS-based detector. Accordingly, the two-layer design reduces complexity of the system and associated cost.

In some embodiments, a product including a medium storing a set of instructions is provided. An execution of the instructions causes an imaging method to be performed. The imaging method includes: obtaining first image signals generated by a first scintillator layer, the first image signals having a first quantum efficiency and a first spatial resolution; obtaining second image signals generated by a second scintillator layer, the second image signals having a second quantum efficiency and a second spatial resolution, wherein the first quantum efficiency is lower than the second quantum efficiency, but the first spatial resolution is higher than the second spatial resolution; and electronically processing the first image signals and the second images by an image combiner to combine the first image signals and the second image signals forming a combined image.

Exemplary Machine

Figure 11:
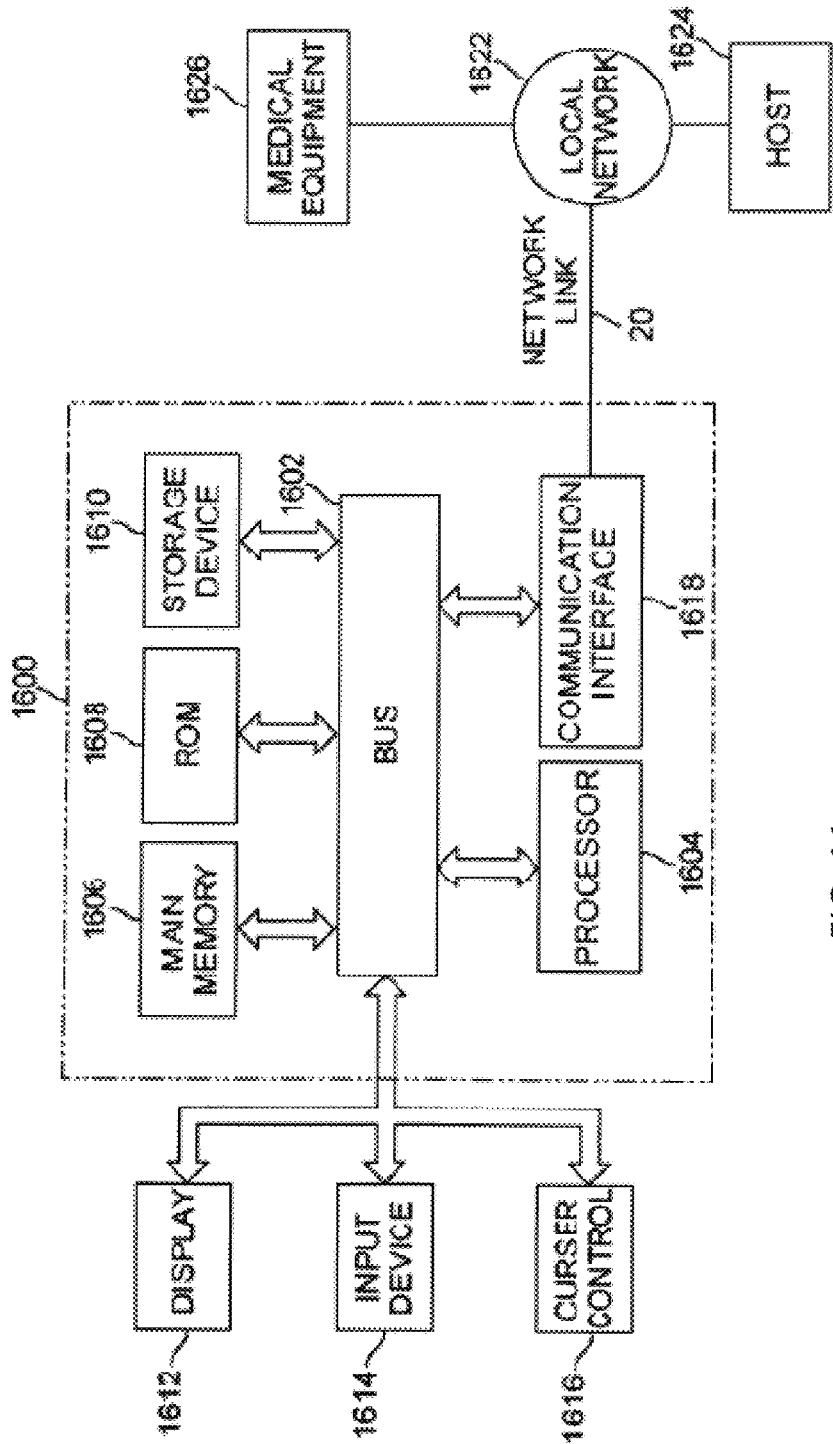
FIG. 11 illustrates a block diagram of a particular machine in accordance with some embodiments.

FIG. 11 is a block diagram illustrating an embodiment of a particular machine 1600 that can be used to implement various features described herein. In some embodiments, the particular machine 1600 may be considered as an example of a processing system. In some embodiments, the processing system 1600 may be used to implement the processing unit 54 of FIG. 1. The processing system 1600 may also be used to implement a control that controls an operation of the imaging apparatus 200, and/or a control that controls an operation of the treatment machine. In further embodiments, the processing system 1600 may be used to implement a component of the imaging apparatus 200, such as the image combiner of the imaging apparatus 200.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk, solid state disk, or optical disk, is provided and coupled to the bus 1602 for storing information and instructions.

The processor system 1600 may be coupled via the bus 1602 to a display 167, such as a flat screen monitor, for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical, solid state or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a flexible disk, hard disk, magnetic tape, or any other magnetic medium, a CD-ROM, any other optical medium, any other physical medium with patterns of holes, a RAM, a PROM, and EPROM, a FLASH-EPROM, solid state disks any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk or solid state disk of a remote computer. The remote computer can load the instructions into its dynamic memory and send the instructions over a network, such as the Internet. The processing system 1600 can receive the data on a network line. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source and/or an imaging device or a switch operatively coupled to a radiation beam source and/or an imaging device. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An imaging apparatus comprising:
a first scintillator layer configured to provide first photons for generating first image signals of a first image with a first quantum efficiency, the fist image having a first spatial resolution;
a second scintillator layer configured to provide second photons for generating second image signals of a second image with a second quantum efficiency, the second image having a second spatial resolution, wherein the first quantum efficiency is lower than the second quantum efficiency, but the first spatial resolution is higher than the second spatial resolution; and
an image combiner configured to combine the first image signals and the second image signals.

2. The imaging apparatus of claim 1, wherein the image combiner is configured to combine the first image signals and the second image signals in a way that increase signal-to-noise ratio while reducing spatial resolution loss.

3. The imaging apparatus of claim 1, wherein the image combiner is configured to combine the first image signals and the second image signals based on frequency-dependent weighting.

4. The imaging apparatus of claim 1, wherein the image combiner is configured to combine the first image signals and the second image signals based on frequency-dependent filtering.

5. The imaging apparatus of claim 1, wherein the image combiner is configured to combine the first image signals and the second image signals based on noise-dependent weighting.

6. The imaging apparatus of claim 1, wherein the image combiner is configured to combine the first image signals and the second image signals in image domain based on noise reduction.

7. The imaging apparatus of claim 1, wherein the image combiner is configured to apply a first weight factor for the first image signals, and a second weight factor for the second image signals.

8. The imaging apparatus of claim 7, wherein the first weight factor is between 0.1 and 0.4.

9. The imaging apparatus of claim 7, wherein the first weight factor has a first value below 0.2 for a first frequency or first frequency range, and a second value above 0.2 for a second frequency higher than the first frequency or for a second frequency range higher than the first frequency range.

10. The imaging apparatus of claim 1, wherein the image combiner is configured to combine the first image signals and the second image signals based on modulation transfer function (MTF).

11. The imaging apparatus of claim 1, wherein the image combiner is configured to combine the first image signals and the second image signals based on noise power spectrum (NPS).

12. The imaging apparatus of claim 1, wherein the image combiner is configured to combine the first image signals and the second image signals based on detective quantum efficiency (DQE).

13. The imaging apparatus of claim 1, wherein the first scintillator layer is GOS-based, and wherein the second scintillator layer is glass-based.

14. The imaging apparatus of claim 1, wherein the first scintillator layer and the second scintillator layer are stacked.

15. The imaging apparatus of claim 1, further comprising a third scintillator layer, wherein the first scintillator layer, the second scintillator layer, and the third scintillator layer are stacked.

16. The imaging apparatus of claim 15, further comprising a fourth scintillator layer, wherein the first scintillator layer, the second scintillator layer, the third scintillator layer are stacked, and the fourth scintillator layer are stacked.

17. The imaging apparatus of claim 15, wherein the image combiner is configured to combine third image signals associated with the third scintillator layer with the first image signals and the second image signals.

18. The imaging apparatus of claim 1, wherein the imaging apparatus is configured to provide a detective quantum efficiency of 5% or higher.

19. An imaging method, comprising:
obtaining first image signals associated with first photons generated by a first scintillator layer, the first image signals generated with a first quantum efficiency and forming a first image having a first spatial resolution;
obtaining second image signals associated with second photons generated by a second scintillator layer, the second image signals generated with a second quantum efficiency and forming a second image having a second spatial resolution, wherein the first quantum efficiency is lower than the second quantum efficiency, but the first spatial resolution is higher than the second spatial resolution; and
electronically processing the first image signals and the second images by an image combiner to combine the first image signals and the second image signals forming a combined image.

20. A product having a medium storing a set of instructions, an execution of which causes an imaging method to be performed, the imaging method comprising:
obtaining first image signals associated with first photons generated by a first scintillator layer, the first image signals generated with a first quantum efficiency and forming a first image having a first spatial resolution;
obtaining second image signals associated with second photons generated by a second scintillator layer, the second image signals generated with a second quantum efficiency and forming a second image having a second spatial resolution, wherein the first quantum efficiency is lower than the second quantum efficiency, but the first spatial resolution is higher than the second spatial resolution; and
electronically processing the first image signals and the second images by an image combiner to combine the first image signals and the second image signals forming a combined image.

* * * * *